United States Patent [19]
Bergersen

[11] Patent Number: 4,898,535
[45] Date of Patent: Feb. 6, 1990

[54] SELF-OPENING PREFORMED ACTIVATOR AND POSITIONER

[76] Inventor: Earl O. Bergersen, 950 Green Bay Rd., Winnetka, Ill. 60093

[21] Appl. No.: 180,178

[22] Filed: Apr. 11, 1988

[51] Int. Cl.⁴ .............................................. A61C 7/00
[52] U.S. Cl. ......................................................... 433/6
[58] Field of Search ................... 433/5, 6, 19; 128/861

[56] References Cited

U.S. PATENT DOCUMENTS

| | | | |
|---|---|---|---|
| 3,536,069 | 10/1970 | Gores | 433/6 |
| 3,848,335 | 1/1974 | Bergersen | 433/6 |
| 3,898,736 | 8/1975 | Bergersen | 433/6 |
| 3,939,598 | 1/1975 | Bergersen | 433/6 |
| 3,950,851 | 4/1976 | Bergersen | 433/6 |
| 4,073,061 | 2/1978 | Bergersen | 433/6 |
| 4,139,944 | 2/1979 | Bergersen | 433/6 |
| 4,505,672 | 3/1985 | Kurz | 433/6 |

Primary Examiner—Robert Peshock
Attorney, Agent, or Firm—Hill, Van Santen, Steadman & Simpson

[57] ABSTRACT

A removable orthodontic appliance is provided with a means for retaining the appliance within the user's mouth. The appliance has an upper and lower tooth receiving trough and the troughs are separate at an anterior end, but connect at a posterior end by a resilient hinge which biases the appliance into an open position with the two trough anterior ends urged apart. Such an appliance can be manufactured by slitting the appliance after molding, before it has cooled, to thermoset the hinge in an open position; slitting the appliance after it has cooled, reheating the hinge area and then thermosetting it in an open position; or molding the appliance in an open position.

12 Claims, 1 Drawing Sheet

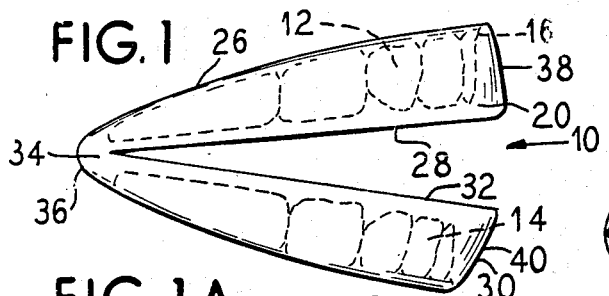
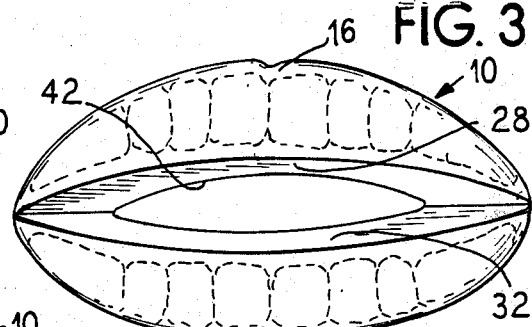
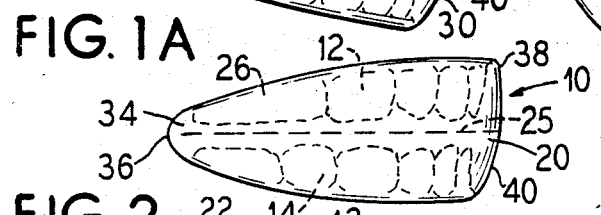
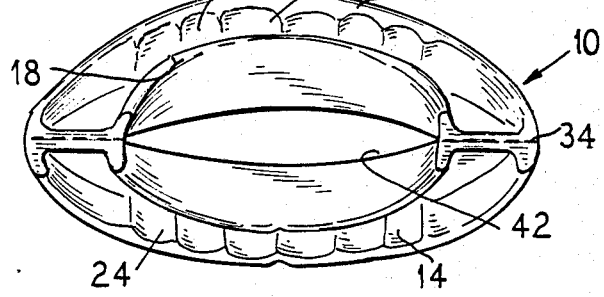
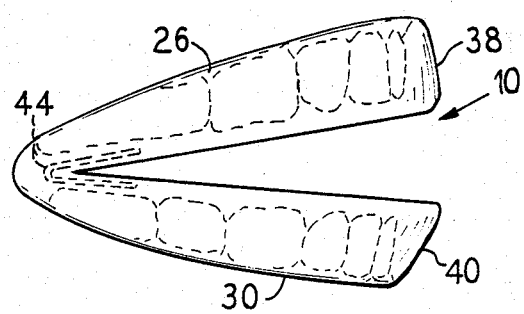
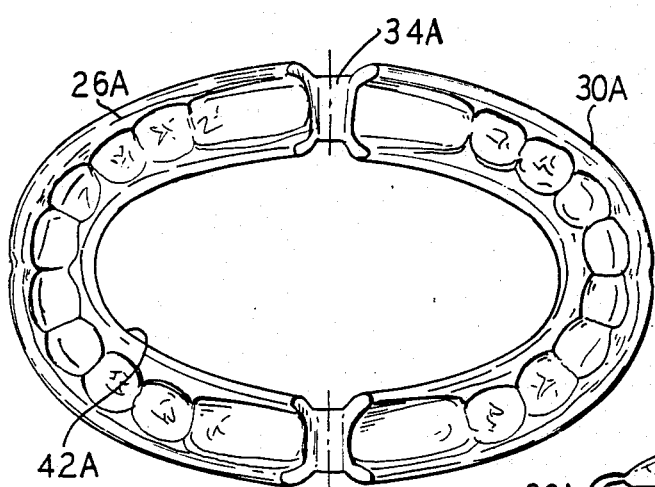
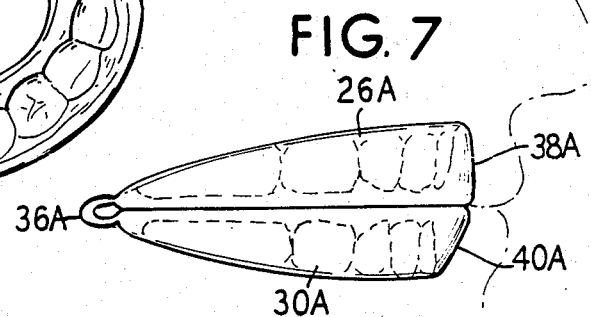
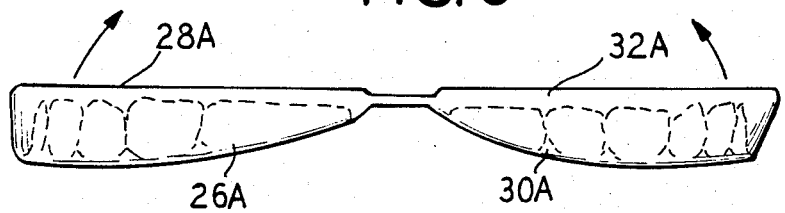

SELF-OPENING PREFORMED ACTIVATOR AND POSITIONER

BACKGROUND OF THE INVENTION

Field of the Invention

The present invention relates to an orthodontic appliance or positioner.

Children, particularly those at a young age (e.g. at 3-7 years) frequently have habits such as playing with their tongue and lips as well as mouth breathing habits when they sleep and approximately 60% of young children have a hard time keeping standard removable orthodontic appliances, such as those described in my U.S. Pat. Nos. 3,848,335 and 3,939,598, in their mouths at night. This is because when they open their mouths unconsciously, the appliance has a tendency to fall out. When the child gets older (from about 8-10 years) about 80% will keep the appliance in their mouth all night, while from 11 years on, about 95% normally keep it in their mouths all night during sleeping hours.

Thus, it would be an improvement and benefit to the art if a removable appliance would be provided with a means for retaining the appliance within the mouth to prevent dislodging of the appliance during sleeping hours.

SUMMARY OF THE INVENTION

The present invention provides for an improved orthodontic appliance of the removable type which overcomes the problems of the standard removable appliances. This device includes a means for retaining the appliance within the mouth, that means being an arrangement for biasing an upper portion of the appliance into contact with the upper row of teeth and biasing a lower portion of the appliance in contact with lower row of teeth towards those teeth so that the appliance will continuously be held in place. A structure particularly suitable to carrying out this invention has the upper and lower portions of the appliance generally separate, but has a hinged connecting portion at a posterior end of the appliance. The hinge portion is formed such that the device is self-opening, that is the anterior portions are urged away from each other.

Such a device can be constructed by sliting the plastic or other resilient material appliance along a center parting line (along the direction of the occlusal plane) either at the time of molding or afterwards. If the slit is made at the time of molding, the appliance is immediately spread open and the molded plastic is allowed to cool and thermoset in an opened position so that it takes force to reclose it. The resiliency of the appliance will cause the appliance to be self-opening.

Another method of constructing such an appliance requires the appliance to be cold slit along the same center parting line after the appliance has been molded and has cooled and held open while the plastic at the "hinge" portion is heated up slightly and allowed to thermoset in the opened position. The severity of the cut towards the back or posterior section of the appliance provides for either a weak (further posterior cut) or a strong force to close the appliance on the part of the patient.

The advantages of such an appliance are not only to increase the number of children who can normally keep it in their mouths at night but also to place a slight depressive force against the anterior (front) teeth in order to correct deep or severe overbites while the users have the appliance in their mouths. This depressive force can also be increased by inserting a flexible and resilient metal plate or spring as a hinge to increase the force necessary to close the mouth when the appliance is in the mouth.

Another advantage of the appliance where the piece is molded with the two halves separated in a flat position with an integral injection molded hinge in between, is that different configurations of dies can be placed in combination with each other as well as moved forward or backward in relation to the bendable portion of the hinge in order to increase or decrease the distance or relation antero-posteriorally (front to back) and thereby create different types of appliances that can correct different severities of malocclusion such as severe class II, mild class II, class I or III malocclusions. The hinge portion can also be made thicker or thinner, or wider or narrower, to increase or decrease the force of the hinge.

BRIEF DESCRIPTION OF THE DRAWINGS

FIG. 1 is a side elevational view of an appliance embodying the principles of the present invention.

FIG. 1A is a side elevational view of the appliance of FIG. 1 prior to slitting.

FIG. 2 is a lingual view of the appliance shown in FIG. 1.

FIG. 3 is a front labial view of the device shown in FIG. 1.

FIG. 4 is a side elevational view of an alternative embodiment of the device shown in FIG. 1.

FIG. 5 is a perspective view of a metal spring added to the appliance as shown in FIG. 4.

FIG. 6 is an alternative embodiment of the device shown in an open top view.

FIG. 7 is a side elevational view of the device of FIG. 6 shown in a closed position.

FIG. 8 is a side elevational view of the device of FIG. 6 shown in an open position.

DETAILED DESCRIPTION OF THE PREFERRED EMBODIMENTS

FIGS. 1-3 illustrates a positioner 10 which includes an upper trough 12 for receiving the maxillary or upper row of teeth, and a lower trough 14 for receiving the mandibular or lower row of teeth. The troughs are formed generally by a labial-buccal flange 16 and a lingual flange 18. The flanges are connected by an isthmus portion 20. Both the upper and lower troughs are provided with tooth receiving depressions or sockets 22, 24. The appliance is partially split along a central parting line 25 (FIG. 1A) such that the upper trough 12 is in an upper portion 26 having a solid lower surface 28 formed by the slit and the lower trough 14 is in a lower portion 30 having an upper surface 32 formed by the slit. A connecting hinge portion 34 is formed at a posterior end 36 of the appliance since the slit extends only partially through the appliance thus leaving an anterior end 38 of the upper part 26 and an anterior end 40 of the lower part 30 separate from each other.

The lower surface 28 of the upper part 26 and the upper surface 32 of the lower part 30 do not extend completely back to the hinge 34 thereby leaving an aperture 42 centered at the hinge in those two walls which acts an air flow passage to permit the user to breathe through this opening when the appliance is in the user's mouth.

This appliance can be manufactured by several different methods. In a first method, the appliance is molded as a single piece with the upper part 26 integral and coextensive with the lower part 30 (see FIG. 1A), but at the time of molding a slit is made along a portion of the center parting line 25 from the anterior end 38, 40 back toward the posterior end 36 leaving only a portion of the appliance unslit, thus resulting in the hinge portion 34. After the sliting has occurred, the appliance is immediately spread open so that the lower surface 28 of the upper part 26 and the upper surface 32 of the lower part 30 generally form a single plane, and then the appliance is allowed to cool and thermoset in this opened position. Due to this thermoset, the resilience of the appliance material will cause the appliance to self-open, that is the anterior ends 38, 40 of the upper and lower portion will be continuously urged away from each other. The self-opening force can be adjusted by changing the length of the slit, and thus the amount of hinge area, with a longer slit and lesser hinge area resulting in a lower self-opening force.

A second method for manufacturing such an appliance would be to again mold the appliance such that the top portion 26 and lower portion 30 are integrally formed and after the appliance has cooled, the slit can be made, again along the parting line 25, and with the appliance held in an open position the hinge portion 34 can be reheated and then allowed to thermoset in the open position.

FIGS. 4 and 5 illustrate an alternative embodiment in which it is possible to increase the self-opening force by inserting a flexible metal plate or spring in the hinge area, preferably during the molding process, the metal spring being preformed in a semi-opened position to urge the anterior ends 38, 40 of the appliance apart. The spring constant for the spring can be selected to provide the desired self-opening force for the appliance.

An alternative embodiment of the positioner is illustrated in FIGS. 6–8 in which the appliance is manufactured by injection molding wherein an upper part 26A is initially formed as a distinct and separate part of the appliance from the lower part 30A. A hinge portion 34A is also formed during the molding process and this hinge portion 34A interconnects the upper portion 26A and lower portion 30A. This appliance is molded and cooled in the opened position as shown in FIGS. 6 and 8 and, thus due to the resiliency of the plastic material of the appliance, will tend to self-open when the appliance is being worn as shown in FIG. 7.

Again, a lower surface 28A of the upper part 26A and an upper surface 32A of the bottom part 30A do not cover the entire area of the appliance and thus, leave an opening 42A through which the user may breathe while wearing the appliance.

As is apparent from the foregoing specification, the invention is susceptible of being embodied with various alterations and modifications which may differ particularly from those that have been described in the preceeding specification and description. It should be understood that I wish to embody within the scope of the patent warranted hereon all such modifications as reasonably and properly come within the scope of my contribution to the art.

I CLAIM AS MY INVENTION:

1. An orthodontic appliance for use in the positioning of teeth which includes a first tooth receiving trough in an upper portion for positioning an upper row of teeth and a second tooth receiving trough in a lower portion for positioning a lower row of teeth, said troughs being defined by lingual and labial-buccal flanges and including an isthmus interconnecting said flanges, said upper portion isthmus and said lower portion isthmus being separated at an anterior end of said appliance, but connected at a posterior end of said appliance to form a hinge connection between said two portions.

2. An orthodontic appliance according to claim 1, wherein said appliance is constructed of a resilient material and said hinge portion continuously urges said upper portion and lower portion apart.

3. An orthodontic appliance according to claim 1, wherein a resilient spring member is incorporated into said hinge portion to continuously urge said upper and lower portions apart.

4. An orthodontic appliance according to claim 1, wherein an opening is formed at said posterior end of said appliance to permit a user to breathe through said opening.

5. An orthodontic appliance for use in positioning or straightening teeth which includes a first tooth receiving trough in an upper portion for positioning an upper row of teeth and a second tooth receiving trough in a lower portion for positioning a lower row of teeth, said troughs being defined by lingual and labial-buccal flanges and including an isthmus interconnecting said flanges, and resilient means interconnecting a posterior end of said upper and lower portions wherein anterior ends of said upper and lower portions are continuously urged apart.

6. An orthodontic appliance according to claim 5, wherein said appliance is molded from a resilient material and said resilient means comprises a hinge portion of the same material as said appliance, being molded concurrently and integrally with said appliance.

7. An orthodontic appliance according to claim 5, wherein said resilient means comprises at least one metallic spring member interconnecting said posterior ends of said upper and lower portions.

8. An orthodontic appliance according to claim 5, wherein an opening is formed at said posterior end of said appliance to permit a user to breathe through said opening.

9. A removable orthodontic appliance for use in the positioning of teeth which includes a first tooth receiving trough in an upper portion for positioning an upper row of teeth and a second tooth receiving trough in a lower portion for positioning a lower row of teeth, said troughs being defined by lingual and labial-buccal flanges and including an isthmus interconnecting said flanges, and means for retaining the appliance within a mouth of a user, said retaining means comprising means for continuously biasing said first tooth receiving slot against the upper row of teeth and said second tooth receiving slot against the lower row of teeth for all positions of the user's mouth in the form of a resilient hinge area interconnecting a posterior end of said isthmus.

10. A removable orthodontic appliance according to claim 9, wherein said appliance is formed from a resilient material and said hinge area is formed integrally with and of the same material as the remainder of said appliance.

11. A removable orthodontic appliance according to claim 9, wherein a resilient spring member is incorporated into said hinge area.

12. A removable orthodontic appliance according to claim 9, wherein an opening is formed in said appliance to permit a user to breathe through said opening.

* * * * *